US006263008B1

(12) United States Patent
Lai

(10) Patent No.: US 6,263,008 B1
(45) Date of Patent: Jul. 17, 2001

(54) OVER-SAMPLING DETECTOR ARRAY AND RE-SAMPLING TECHNIQUE FOR A CONE-BEAM COMPUTED TOMOGRAPHY SYSTEM

(75) Inventor: Ching-Ming Lai, Wakefield, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 09/375,151

(22) Filed: Aug. 16, 1999

(51) Int. Cl.[7] .................................................. A61B 6/03
(52) U.S. Cl. .............................. 375/19; 378/15; 378/901
(58) Field of Search ................................ 378/4, 15, 19, 378/901

(56) References Cited

U.S. PATENT DOCUMENTS

| | | | |
|---|---|---|---|
| 5,430,783 | 7/1995 | Hu et al. | 378/15 |
| 5,796,803 | 8/1998 | Flohr et al. | 378/15 |
| 5,802,134 | 9/1998 | Larson et al. | 378/4 |
| 6,148,056 | * 11/2000 | Lin et al. | 378/4 |

OTHER PUBLICATIONS

Feldkamp et al., "Practical Cone–Beam Algorithm", J. Opt. Soc. Am. A/vol. 1, p612, No. 6, Jun. 1984.

* cited by examiner

Primary Examiner—David V. Bruce
(74) Attorney, Agent, or Firm—McDermott, Will & Emery

(57) ABSTRACT

An over-sampling detector array employs a plurality of rows of detectors, the height of each of the rows in use for a helical scan being smaller than the intended slice thickness for reconstruction. Over-sampled collected projection data are re-sampled along the translation axis according to the slice thickness. As a result, the slice profile is enhanced and the projection data are more consistent from all view angles, leading to an improvement in image resolution along the translation axis and fewer reconstruction artifacts in the image. The detector array may have the same row height for all rows, or may have different row heights in different rows. Data collected by rows of height equal to or less than the slice thickness are used for reconstruction. In a preferred embodiment, the heights of the detectors of outer rows increase progressively and gradually with respect to the height of the middle rows. In a preferred re-sampling technique, the data are first integrated from successive rows. The re-sampling data are then calculated as the difference of the integrated data between the locations of the slice boundaries along the translation axis.

24 Claims, 6 Drawing Sheets

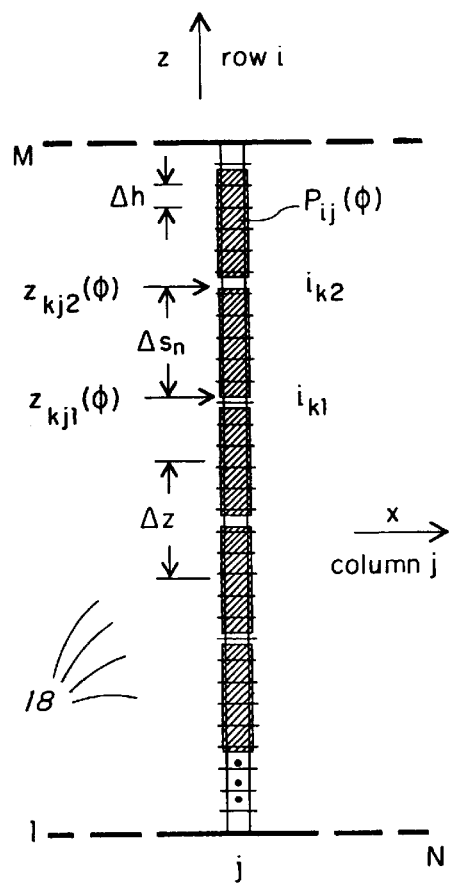 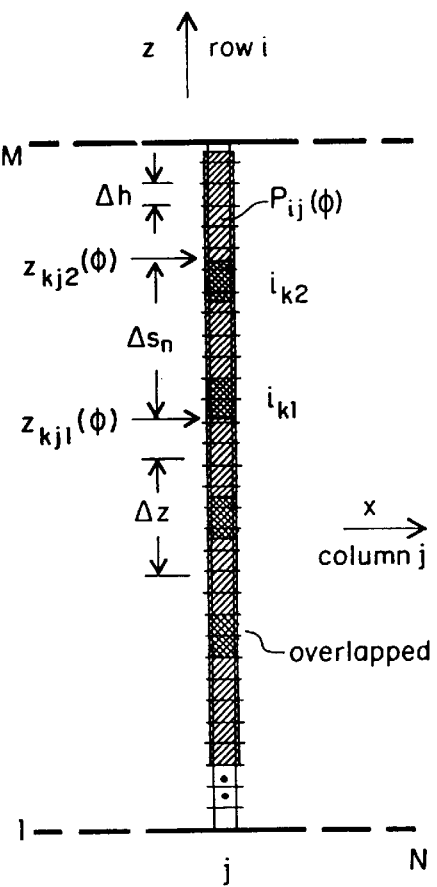
*FIG. 3*  *FIG. 4*

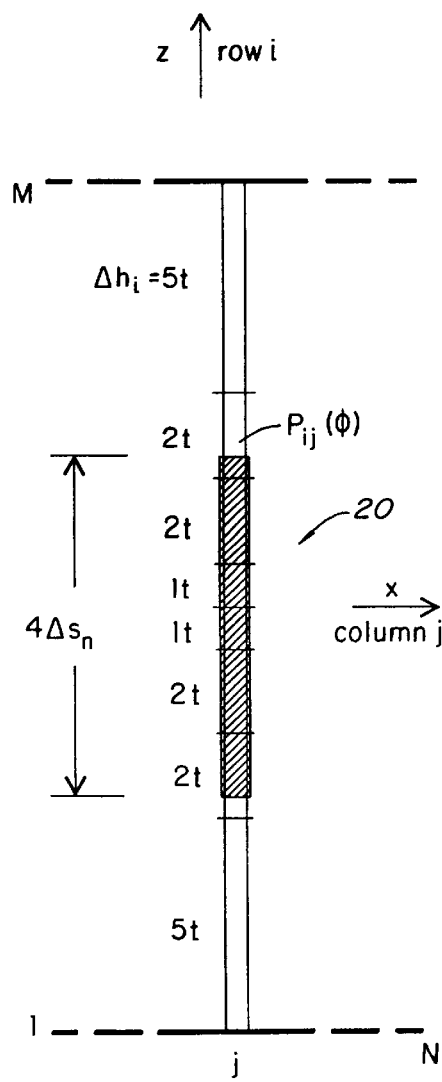
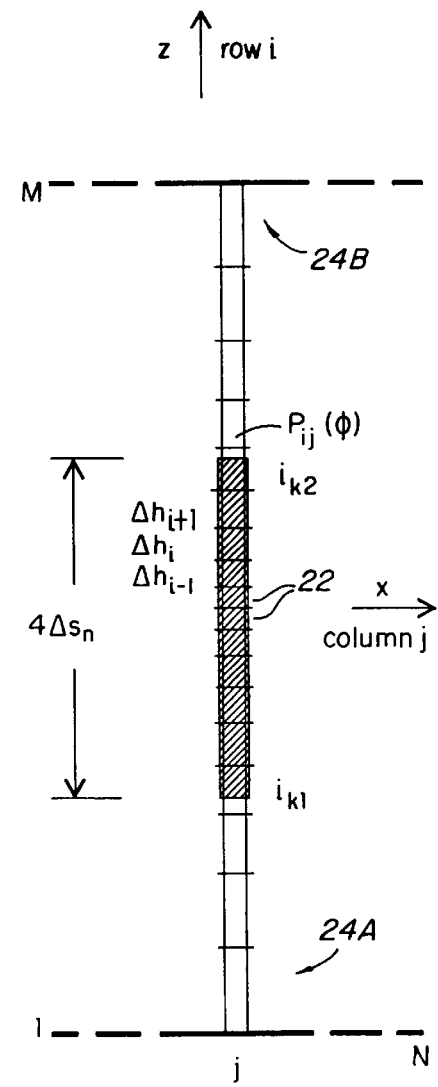
*FIG. 5*  *FIG. 6*

OVER-SAMPLING DETECTOR ARRAY AND RE-SAMPLING TECHNIQUE FOR A CONE-BEAM COMPUTED TOMOGRAPHY SYSTEM

BACKGROUND OF THE INVENTION

In an X-ray computed tomography (CT) system, an energy source irradiates X-ray beams through an object, and a detector array senses and measures the intensity of the attenuated X-ray beams across a thin section of the object. The X-ray beam intensity level incident at each detector is digitized and converted to a value representing the line integral, referred to in the art as a "projection", of the object along the X-ray beam path.

In a stationary scan configuration, or "non-helical" scan mode, the object is fixed in position during each scan, while in a translational scan, or "helical" scan mode, the object translates in the same direction as the axis of rotation (z-axis) during a scan, improving system throughput.

For third-generation CT systems, during a scan, an X-ray source and a detector array are mounted on a gantry and rotate together about an object. Successive sets of projections of the object are recorded at incremental gantry rotation angles. At each rotation angle, the collected projections represent a projection profile of the object at that angle. With a set of projection profiles over many view angles, an image of the object across the scanned section, or "slice", can be generated in a process known as reconstruction, which involves a convolution and back projection of the collected projections.

In a "conventional" CT system, the detector array comprises a single-row detector array, while a "cone-beam" CT system employs a two-dimensional detector array typically having multiple rows and multiple columns of detectors. A cone-beam CT system allows for multiple slices of an object to be scanned simultaneously. An example of a non-helical cone-beam scan technique is described in Feldkamp et al., "Practical Cone-Beam Algorithm", J. Opt. Soc. Am. A/Vol 1, p612, No. 6, June 1984. An example of a helical cone-beam scan is described in U.S. Pat. No. 5,430,783, issued Jul. 4, 1995 to Hu, et al.

With reference to FIG. 1, which is a schematic diagram of a cone-beam system, if the height (the length along the z-axis) of the ith detector row is $\Delta H_i$, then the equivalent scaled height $\Delta h_i$ of the detector row at isocenter 14 (in this case, assume the isocenter to be along the z-axis) is:

$$\Delta h_i = \Delta H_i R/D \quad (1)$$

where R and D represent distances from the X-ray focal spot 10 to the detector array 12 and from the x-ray focal spot 10 to the system isocenter 14, respectively; and the ratio R/D represents scaling factor.

In an "equal height" detector system for a cone-beam scanner, row heights $\Delta H_i$ are the same for all rows of detectors 1 ... M. In a "non-equal height" detector system, the rows may be of different heights. In one such non-equal height system, the individual row heights $\Delta H_i$ are configured according to certain integer multiples such that adjacent rows can be combined to provide the equivalent of an effective constant group height $\Delta H$. For example, assuming a multiple-row detector array having 8 individual rows of respective detector heights: 5t, 2t, 2t, 1t, 1t, 2t, 2t, 5t, as shown in FIG. 5, the data collected at particular row groupings of the array can be combined to become 4 rows of detectors at a constant height of $\Delta H$ 5t (i.e., combined to 5t, 2t+2t+1t, 1t+2t+2t, 5t, respectively). A number of additional combinations can also be realized. This type of detector configuration is disclosed in U.S. patent application Ser. No. 09/159,067, filed Sep. 23, 1998, commonly owned with the present application, and incorporated herein by reference.

In a non-helical scan cone-beam CT system, the resolution of the reconstructed image along the z-axis, which in turn is referred to herein as the "slice width" or "slice thickness", is determined by the detector height at isocenter 14, $\Delta h_i$. This is analogous to the slice thickness of a conventional CT system having a single row of detectors, except that in the cone-beam system multiple slices are scanned simultaneously by the multiple rows. In the preceding example with four groups of rows at a constant group height of detection of $\Delta H=5t$, all four slices will exhibit the same slice thickness of $\Delta h=5t$ R/D.

However, for a helical scan, effective slice thickness broadens considerably. This is due to the fact that data for each slice is acquired by different rows or groups of rows of detectors during the course of the helical scan. At each view angle, data for each slice is, in general, acquired by either one or two rows or groups of rows of detectors due to translation of the object during a scan, and effective height of detection is thus varied between one and two rows or groups of rows of detectors. Consequently, the slice thickness of a helical scan is considerably broadened, as compared to a non-helical scan. Furthermore, the effective height of detection is inconsistent, in that it varies with view angle. Reconstruction artifacts are thus introduced due to variation in the effective height of detection at the multiple view angles.

In this manner, the slice profile is not sharply defined due to broadening of the detection, and the reconstructed image is prone to contain artifacts due to inconsistency of the projection data. To reduce the broadening of the slice, it has been suggested to first reconstruct multiple thin slices by dividing a row of detectors into a set of multiple sub-rows of detectors, and to independently reconstruct a plurality of sub-slices using the set of multiple sub-rows. This is followed by combining the sub-slices into a single composite slice. Such a technique results in a composite slice having a slice thickness considerably greater than each of the individual sub-slices, but having substantially improved slice profile as described in U.S. Pat. No. 5,430,783, issued Jul. 4, 1995 to Hu et al., incorporated herein by reference. However, this approach is computationally expensive in that it requires multiple convolutions and back projections for each sub-slice.

SUMMARY OF THE INVENTION

To address the shortcomings of the prior techniques, the present invention provides a method of and apparatus for mitigating data inconsistency leading to the reconstruction artifacts described above, and for providing a sharper slice profile having improved precision. An over-sampling detector array and improved re-sampling technique are provided to prepare projection data for reconstruction. The over-sampling detector array employs a plurality of rows of detectors, with the height of each detector row being less than the slice thickness. The improved re-sampling technique involves a re-sampling of the over-sampled data, and combination thereof prior to reconstruction, thereby enhancing resulting image quality in a manner that improves system throughput.

In a first aspect, the present invention is directed to a method of reconstructing an object image as successive slices of a predetermined slice thickness in a helical cone-beam computed tomography scanner. Projection data are over-sampled with a two-dimensional detector array arranged in rows and columns. The detector array includes detector rows each having a height less than the slice thickness. The projection data are re-sampled relative to a system translation axis according to the predetermined slice thickness. The re-sampled projection data are next reconstructed to generate an object image.

Over-sampling may comprise over-sampling projection data with a detector array having row heights that are equal (an "equal-height" detector array) or unequal (a "non-equal-height" detector array). Projection data re-sampling preferably comprises identifying the boundaries of each slice along the translation axis and summing the data values for detector rows between the boundaries. Boundary detector rows containing the boundaries are identified and the projection data collected by the boundary detector rows are weighted according to the relative position of the boundary with respect to the detector row along the translation axis. The locations of multiple slices to be re-sampled are identified and reconstructed at a predetermined interval, such that the reconstructed slices overlap, are contiguous, or are spaced apart, depending on the application. The slice may be substantially orthogonal to the translation axis, or optionally tilted at an oblique angle with respect to the translation axis. In a preferred embodiment, during re-sampling, the projection data values are first integrated from successive rows of detectors, leading to more efficient operation.

The detector rows may be of equal row height, or may comprise a middle row and outer rows, the row height of the outer rows increasing progressively as their distance from the middle row increases. The progressive increase of the outer row heights may be according to integer multiples of the middle row or preferably gradual, or fractional with respect to the height of the middle row.

In a second aspect, the present invention is directed to a detector array for a computed tomography scanner. The detector array includes an array of detector elements arranged in longitudinal columns along a rotation axis, and in lateral rows along a lateral axis orthogonal to the longitudinal axis. The outer rows of the array are of a height that is gradually increased with respect to the inner rows.

In a preferred embodiment, the heights of all detector rows in use for the scan are each shorter than the predetermined slice thickness. The detector rows each preferably lie along an arc lying in a plane substantially orthogonal to the system longitudinal axis. The arc preferably has a center of curvature at the energy source.

BRIEF DESCRIPTION OF THE DRAWINGS

The foregoing and other objects, features and advantages of the invention will be apparent from the more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 3 is a schematic diagram of the jth column of an equal-height detector array wherein the projection data of multiple slices of nominal slice thickness $\Delta s_n$ are collected by the detectors drawn in shade, in accordance with the present invention.

FIG. 4 is a schematic diagram of the jth column of a multiple row equal-height detector array wherein the nominal slice thickness $\Delta s_n$ is greater than the interval $\Delta z$ between adjacent slices; accordingly, projection data are overlapped between adjacent slices, in accordance with the present invention.

FIG. 5 is a schematic diagram of the jth column of a multiple-row detector array having non-equal height geometry arranged in heights corresponding to a simple integer ratio.

FIG. 6 is a schematic diagram of the jth column of a multiple-row non-equal height detector array having a gradual increase in detector row height with respect to the central row or rows, in accordance with the present invention.

DETAILED DESCRIPTION OF PREFERRED EMBODIMENTS

In CT systems employing a two-dimensional equal-height detector array having rows 1 . . . M of detectors of the same height $\Delta H$, projection data are sampled at a constant spatial interval $\Delta h$ at the isocenter along the z-axis. In the prior techniques described above, multiple slices are reconstructed from the collected data at the nominal slice thickness of $\Delta s_n$, equal to the constant spatial interval $\Delta h$, where the nominal slice thickness is the intended slice thickness predetermined for a given scan. Assuming a helical scan, because the object continuously translates along the z-axis relative to the gantry, the projections contributing to each reconstructed slice are collected by different detector rows at different times. Accordingly, the projection values for each slice are interpolated from the data collected by adjacent detector rows. This interpolation can be performed prior to, or during, the back-projection operation of image reconstruction. The interpolation can be regarded as a weighted average of projection data from two adjacent rows.

Due to this z-axis interpolation, the actual slice thickness, $\Delta s$, in the resulting image, is greater than the nominal slice thickness $\Delta s_n$. As described above, the Hu, et al technique attempts to address the issue of narrowing the slice profile, but does so in a manner that is computationally intensive. More importantly, the interpolation ratio of weighting in averaging from two adjacent rows varies with view angle, which renders the interpolated projection data somewhat inconsistent at different view angles. As a result of such inconsistency, artifacts are introduced into the reconstructed image of the slice.

Figure 1:
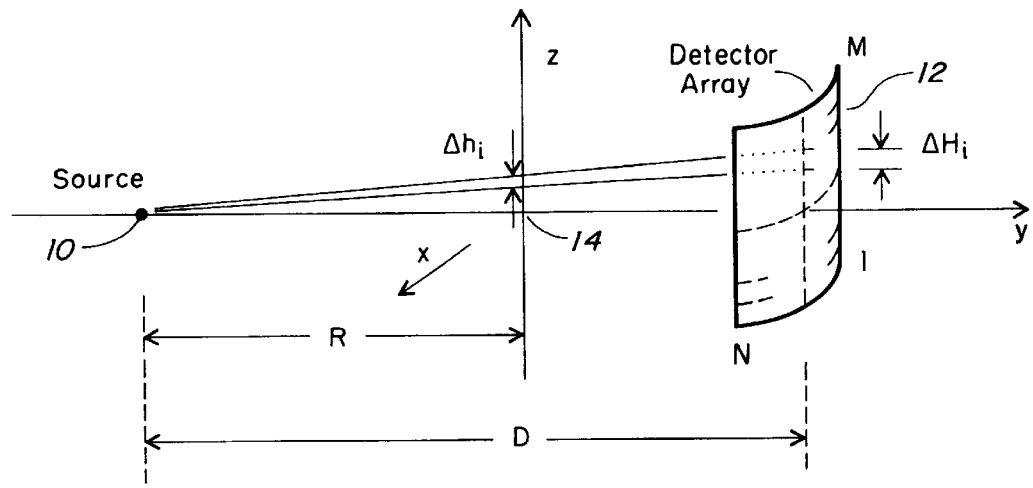
FIG. 1 is a schematic view of an X-ray CT scanner having multiple rows of detectors, wherein the equivalent height of a detector row along the rotation axis $\Delta h_i$ is proportional of the ith row of detectors $\Delta h_i$ by the factor RID.
Figure 2:
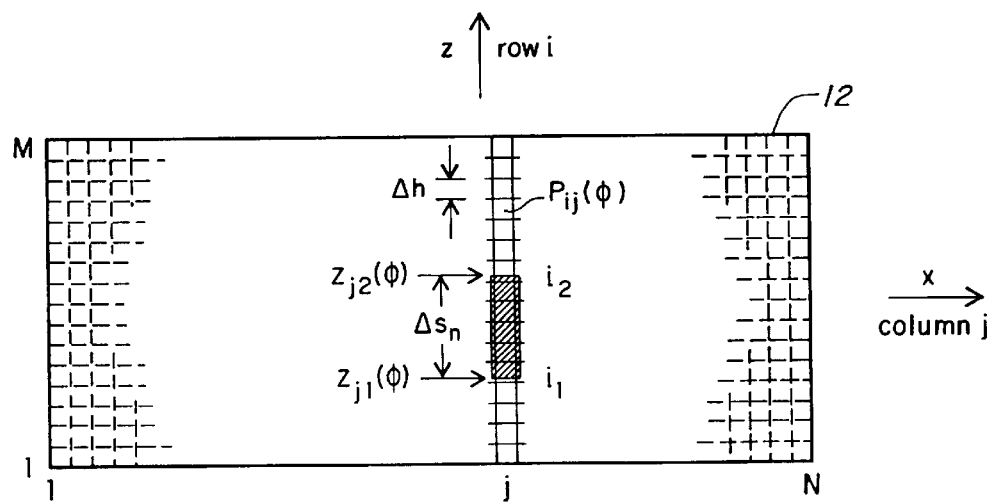
FIG. 2 is a front view of a detector array having rows of equal height ($\Delta h$ measured along the rotation axis) wherein projection data for a single reconstruction slice of thickness $\Delta s_n$ are collected by the shaded column j detectors, in accordance with the present invention.

In contrast, the technique of the present invention re-samples the collected projection data along the z-axis according to the nominal slice thickness $\Delta s_n$. The projection data are preferably re-sampled in each column of detectors independent of other columns as shown in FIG. 2. The row location for the re-sampling can vary with the column location, if oblique slices are selected for reconstruction or the fan-beam projection data collected from each row of detectors are reordered into parallel-beam projection data. Thus, in general, the z-position for the re-sampling is different for each column at each view angle $\phi$, but can be determined from the detector geometry.

For example, in FIG. 2, which is a front view of the detector array 12 along the y-axis, with the detector array flattened for purpose of illustration, the detector array consists of M rows of equal height and N columns of equal width. At a particular view angle $\phi$, the projection value collected by the detector at the ith row and the jth column is denoted as $P_{ij}(\phi)$. The projection of the nominal slice on the detector array at this view angle is centered about $z_j(\phi)$ over a length of $\Delta s_n$, with:

$$z_j(\phi)=z_j(0)+p\phi/2\pi, \quad (2)$$

where p is the pitch, or translation rate, of the system during a helical scan. Thus, the corresponding projection value of the nominal slice $\Delta s_n$ at column j is the sum of the projection values ranging from $z_{j1}(\phi)$ to $z_{j2}(\phi)$ with:

$$z_{j1}(\phi)=z_j(\phi)-0.5\ \Delta s_n, \text{ and} \quad (3)$$

$$z_{j2}(\phi)=z_j(\phi)+0.5\ \Delta s_n. \quad (4)$$

Suppose $z_{j1}(\phi)$ and $z_{j2}(\phi)$ are located at a position along the z-axis within rows $i_1$ and $i_2$, respectively. In this case, the projected region of the nominal slice on the detector column j is extended between rows $i_1$ to $i_2$ as highlighted in the shaded area of FIG. 2. The projection value of the nominal slice $S_j(\phi)$ comprises the sum of projection data values $P_{ij}(\phi)$ measured by the detectors occupying the shaded region. Since the two detectors in rows $i_1$ and $i_2$ are only partially included in this region, a weighting factor wi can be employed to express $S_j(\phi)$ as:

$$S_j(\phi) = \sum_{i=i_1}^{i_2} w_i P_{ij}(\phi) \quad (5)$$

with $w_i$=1.0 for i>$i_1$ and i<$i_2$,
and 0<$w_i$<1.0 for i=$i_1$ or i=$i_2$.

Based on the positions of $z_{j1}(\phi)$ and $z_{j2}(\phi)$ calculated from Equations (3) and (4), and the known isocenter detector height $\Delta h$, the two partial weighting factors $w_{i1}$ and $w_{i2}$ can be determined.

When the nominal slice thickness $\Delta s_n$ is substantially greater than the detector height at isocenter $\Delta h$, the inconsistency of the re-sampled projection data among different views is highly reduced. Consequently, image artifacts caused by inconsistent projection data from different views are highly reduced, and an improvement in the slice profile definition is realized. As compared to the prior technique described above, the re-sampling procedure of the present invention is relatively simplified, and reconstruction is performed on only a single slice, substantially reducing the required computations. For example, assuming that the nominal slice thickness $\Delta s_n$ is a factor m of the detector height at isocenter $\Delta h$, $\Delta s_n$=m $\Delta h$, the prior technique requires reconstruction of m sub-slices for a single slice of interest. In contrast, the present invention first re-samples and combines the data before reconstruction, and therefore only requires a single reconstruction step, thereby reducing the amount of computations by m times in obtaining the nominal slice.

For the special case where the nominal slice thickness and detector height at isocenter are equal, i.e., $\Delta s_n$=$\Delta h$, the re-sampling of projection data is equivalent to the prior z-axis interpolation of projection data from two adjacent detector rows. In this special case, the collected data are not over-sampled.

For the sake of simplicity, only a single nominal slice is re-sampled in the above description. In a preferred embodiment, multiple slices are re-sampled at each view angle. Of course, the total detector height at isocenter, M$\Delta h$, must be greater than the nominal slice thickness $\Delta s_n$ for re-sampling of multiple slices. Suppose the collected projection data are re-sampled into L slices, there are L central positions, $z_{kj}(\phi)$ with k=1, 2, . . . , L, to be calculated. The central positions of adjacent slices are related by:

$$z_{k+1j}(\phi)=z_{kj}(\phi)+\Delta z, \quad (6)$$

where $\Delta z$ is the spatial interval of the multiple slices.

Similar to Equations (3) and (4) above, the boundary positions of each slice are calculated as:

$$z_{kj1}(\phi)=z_{kj}(\phi)-0.5\ \Delta s_n, \text{ and} \quad (7)$$

$$z_{kj2}(\phi)=z_{kj}(\phi)-0.5\ \Delta s_n, \text{ and} \quad (8)$$

for k=1, 2, . . . , L. Assume that slice boundary positions $z_{kj1}(\phi)$ and $z_{kj2}(\phi)$ are located in rows $i_{k1}$ and $i_{k2}$, respectively. In this case, applying the above-described re-sampling technique for a single slice, the projection value for the kth slice, $S_{kj}(\phi)$, is re-sampled as:

$$S_{kj}(\phi) = \sum_{i=i_{k1}}^{i_{k2}} w_{ki} P_{ij}(\phi) \quad (9)$$

with $w_{ki}$=1.0 for i>$i_{k1}$ and i<$i_{k2}$
and 0<$w_{ki}$<1.0 for i=$i_{k1}$ or i=$i_{k2}$
where k=1,2, . . . , L. The projection regions of these multiple slices 18 with respect to the detector locations are depicted in FIG. 3.

In the case where the spatial interval of the multiple slices is selected to be equal to the nominal slice thickness $\Delta z$=$\Delta s_n$, the reconstructed multiple slices are considered to be contiguous. Although this is commonly the most appropriate choice, it is sometimes desirable to have an overlap between adjacent slices. To accommodate this configuration for reconstruction of overlapped multiple slices, the spatial interval value is simply selected to be less than the nominal slice thickness $\Delta z$<$\Delta s_n$. FIG. 4 is an illustration of projection regions of overlapped multiple slices against the detector locations for detector column j. Similarly, for some applications, it may be desirable to skip a region between slices. In this case, the spatial interval value is selected to be greater than the nominal slice thickness $\Delta z > \Delta s_n$.

A CT detector system having rows of detectors of variable height is proposed in U.S. patent application Ser. No. 09/159,067, incorporated by reference above. Assume a detector array having eight rows of detectors of heights of 5t, 2t, 2t, 1t, 1t, 2t, 2t, 5t, as shown in FIG. 5. If only the two middle rows are used, the system is equivalent to a two-row detector system with a height of 1t in either row. If these two middle rows are combined and used with the four rows of 2t in height, the system becomes a five-row detector system having detector rows of 2t height. In other configurations, rows can be combined to provide an equal-height row system having detector row heights of 3t, 4t, 5t, or 10t per row. Although the system consists of rows of different heights, the data can be rearranged to give the effect of multiple rows of equal height. The advantage of this non-equal height detector system is that the total number of rows is less than the equal-height detector system. The system can scan multiple slices at various thicknesses as in an equal-height detector system; however, the outer rows are preferably not to be used in a scan if the detector heights are greater than the nominal slice thickness of the scan. Therefore, the number of detector rows in use depends on the nominal slice thickness selected for the scan. For scanning of thinner slices, the number of detector rows in use, which determines the maximum pitch of the helical scan, is less than the number of detector rows used for scanning of thicker slices.

Since the data collected by this detector system are combined in such a manner so as to effectively provide an equal height multiple-row detector, it suffers from the same problems as the equal-height detector systems mentioned above; namely broadening of the slice thickness and projection data inconsistency. However, in this non-equal height detector system, the middle rows are already in over-sampling configuration for nominal slice thicknesses larger than the height at isocenter of the middle row detectors. Therefore, the over-sampling and re-sampling methods in accordance with the present invention are slightly different for this non-equal height system than the aforementioned equal height detector system. Two configurations are described; a first is based on the existing integer-multiple detector geometry wherein the detector row heights increase in quantum increments relative to the center row, and a second is based on an improved progressive detector geometry wherein the detector row heights increase gradually relative to the center row.

In the example given with eight rows of detectors, M=8, each row having a different height at isocenter $\Delta h_i$ in the integer-multiple detector geometry of FIG. 5, the maximum total height of the detector system is:

$$\sum_{i=1}^{M} \Delta h_i = 5t + 2t + 2t + t + t + 2t + 2t + 5t = 20t \quad (10)$$

Assuming the nominal slice thickness height to be equal to the height of the smallest detector row, $\Delta s_n = t$, the system would not operate in an over-sampling mode and the slice broadening and projection data inconsistency limitations would exist in their full extent. However, when the nominal slice thickness is greater than the height of the smallest detector row at isocenter, i.e., $\Delta s_n \geq 2t$, the methods and apparatus of the present invention serve to mitigate these imperfections. In the present technique, the data from the multiple rows are not combined to form data for a thicker slice, but instead are re-sampled according to the location and thickness of the nominal slice. The various formulae of Equations (2) through (9) described above are applicable, with the notion that $P_{ij}(\phi)$ represents the projection data collected by the ith row of detectors at a row-dependent height $\Delta h_i$. The first and last rows, $i_{k1}$ and $i_{k2}$, with partial weighting factors in Equation (9), are calculated based on the row-dependent heights $\Delta h_i$, with i=1, 2, . . . , M. The region 20 of these rows with non-zero weighting factors is illustrated in FIG. 5 in the shaded area for an instance of four contiguous slices.

During a scan, each slice is translated from one end of the detector array to the other. When the slice is proximal to the middle rows of the detector array, where the detector height is smallest, the projection data are highly over-sampled. Since the detector height of the rows increases with increasing distance from the middle rows, the degree of over-sampling decreases as the slice transitions away from the middle rows. In this integer-multiple geometry, the detector height may change drastically at certain outer rows, for example, from 2t to 5t in the last row of the example given above in FIG. 5. This drastic increase in detector height gives a corresponding sudden decrease in over-sampling. Such a decrease is not desirable, as it exaggerates the inconsistency of projection data from different view angles, and introduces artifacts in the reconstructed image as occurring in the prior techniques described above.

In an improved detector system configuration illustrated in FIG. 6, the detector height $\Delta h_i$ gradually increases from a middle detector row 22 toward upper and lower detector rows 24A, 24B. The purpose of this gradual increase in detector row height is to avoid drastic changes in the detector height, and thus alleviate the data inconsistency problem described above. At the same time, like the integer-multiple detector geometry, this configuration reduces the total number of detector rows required for the system. However, if the heights of the outer rows exceed the nominal slice thickness of a scan, they are not used in the scan, and consequently, helical scan pitch is reduced. In this embodiment, the detector row heights are not necessarily related according to an integer ratio, such as 1,2,2,5 in the above example, since the data are not first recombined. So long as all individual row heights $\Delta h_i$ are known, the first and last rows with non-zero weighting factors, $i_{k1}$ and $i_{k2}$, can be determined. Based on this determination, the data can be re-sampled according to the nominal slice thickness as given in Equations (6) through (9). An example of the re-sampling of four contiguous slices from a detector system having a gradually increased row height is shown in FIG. 6.

In the inventive system having a gradually increased detector height, the heights of those rows in the middle region are preferably less than the smallest slice thickness to be reconstructed. In other words, all projection data are over-sampled, even data for the thinnest slices. The total number of rows M and the specific height $\Delta h_i$ in each row determine the extent of over-sampling for a given number of slices at a given slice thickness. The extent of over-sampling is limited only by practical considerations, such that the total number of rows required is not excessive.

In another aspect, the present invention is further directed to a re-sampling apparatus and method that offers improved computing efficiency. The inventive re-sampling technique described above first calculates the boundary positions of each slice with respect to the detector array, ie., $z_{kj1}(\phi)$ and $z_{kj2}(\phi)$. Based on that, the first and last rows with non-zero weighting factor, i.e., $i_{k1}$ and $i_{k2}$, as well as the partial weights $w_{ki}$ at $i=i_{k1}$ and $i=i_{k2}$ are identified. The re-sampled projection data values $S_{kj}(\phi)$ of channel j at projection angle $\phi$ for slice k are then calculated according to the summation given in Equation (9). The integration method described below offers an improved computing procedure.

If the reconstructing slice is tilted at an oblique angle with respect to the z axis, for example, as described in U.S. Pat. No. 5,802,134, commonly owned with the present patent application, and incorporated herein by reference, the locations of $i_{k1}$ and $i_{k2}$ will depend on the channel number j. If re-sampling is performed after the fan-beam projections collected by a detector row are reordered into parallel-beam projections, the locations of $i_{k1}$ and $i_{k2}$ will also depend on the channel number j. When the locations of $i_{k1}$ and $i_{k2}$ are channel-dependent, the calculation of Equation (9) becomes tedious to generate, as the row number for summation varies with channel number, especially for a vector processor. The integration technique presented below further enhances the efficiency of the re-sampling process so as to make the computations suitable for operation on a vector processor.

In the inventive integration method, the projection values $P_{ij}(\phi)$ collected from the jth column of M detectors are first integrated over all rows and stored in accumulators $A_{ij}(\phi)$ as:

$$A_{ij}(\phi)=A_{i-1,j}(\phi)+P_{ij}(\phi), \tag{11}$$

beginning with $A_{0j}(\phi)=0$, and $i=1, 2, \ldots, M$. Re-sampling is then based on the integrated projection values $A_{ij}(\phi)$.

Figure 7A:
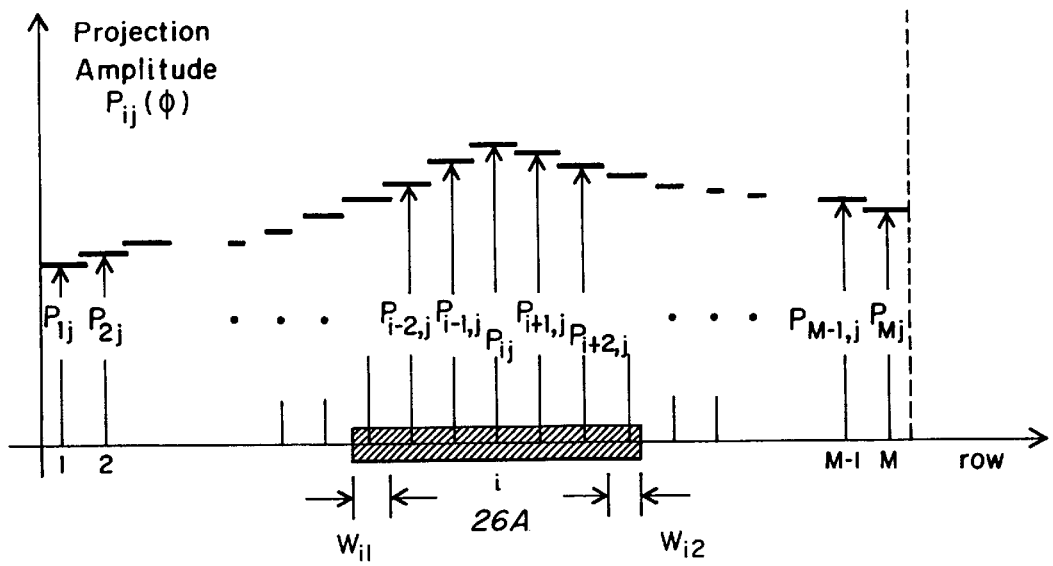
FIG. 7A is a chart of projection data collected by column j of the detector array at a view angle of t, plotted as a function of row number i, wherein rows lying in the range of the nominal slice thickness are indicated by a shaded bar, in accordance with the present invention.
Figure 7B:
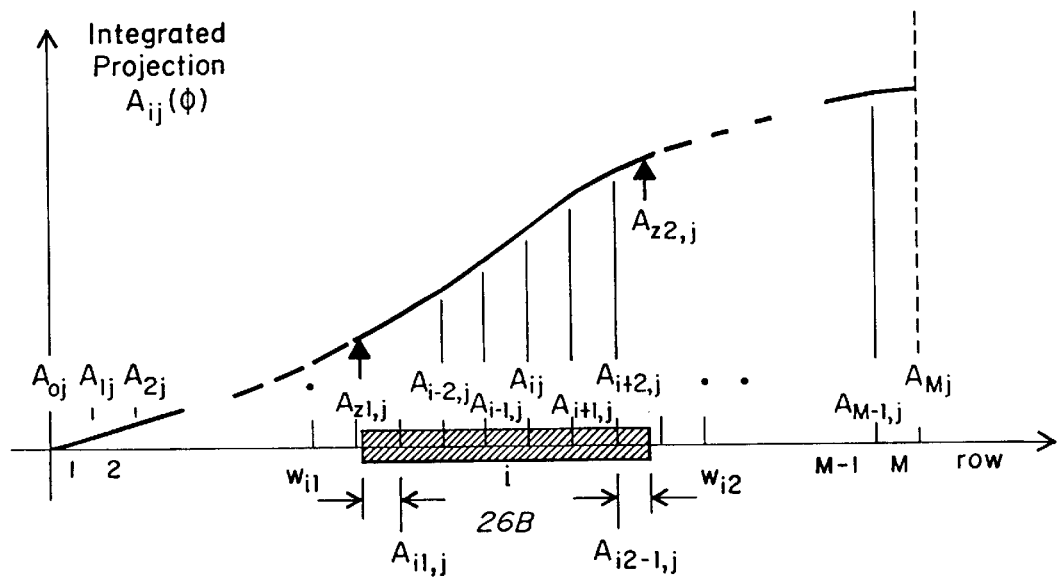
FIG. 7B is a chart of integrated projection data computed from the data given in FIG. 7A, plotted as a function of row number i, in accordance with the present invention.

An example of the original amplitudes $P_{ij}(\phi)$ collected from M rows of equal-height detectors at column j is given in FIG. 7A. The integrated amplitudes $A_{ij}(\phi)$ calculated from Equation (11) are plotted in FIG. 7B for comparison. The shaded areas 26A, 26B indicate the extent of those rows with non-zero weighting factors, and $w_{i1}$ and $w_{i2}$ represent the two partial weights. For simplicity and clarity, only one slice is described and illustrated here for the re-sampling. Therefore, the subscript k is omitted as in Equations (2) through (5). It will be apparent to one skilled in the art of computed tomography that this technique can be readily applied to multiple slices.

The partial weight value $w_{i1}$ is used to interpolate for the starting integrated projection value $A_{z1,j}(\phi)$ as:

$$A_{z1,j}(\phi)+w_{i1-1,j}(\phi)+(1.0-w_{i1})A_{i1,j}(\phi) \tag{12}$$

where the indices i1 and i2 are abbreviated from $i_{k1}$ and $i_{k2}$, respectively, and, in a multiple slice process, depend on the re-sampling slice number k.

Similarly, the second partial weight value $wi_2$ is used to interpolate for the ending integrated projection value $A_{z2,j}(\phi)$ as:

$$A_{z2,j}(\phi)+w_{i2}A_{i2,j}(\phi)+(1.0-w_{i2})A_{i2-1,j}(\phi) \tag{13}$$

The re-sampled projection data values for the kth slice are calculated simply as:

$$S_{kj}(\phi)=A_{z2,j}(\phi)-A_{z1,j}(\phi). \tag{14}$$

Assuming a non-equal height detector row system, at least two alternatives to the integrated method for re-sampling are identified. In a first method, the integrated projection values are generated according to an equal height, that is equal spacing along the z coordinate. If $\Delta h$ represents the quantity divisible by the detector height in every row, the height of any row i can be expressed as $\Delta h_i=m_i\Delta h$, where $m_i$ is an integer. The integrated projection data are generated as:

$$A_{mj}(\phi)=A_{m-1,j}(\phi)+P_{ij}(\phi)/m_i. \tag{15}$$

Figure 8A:
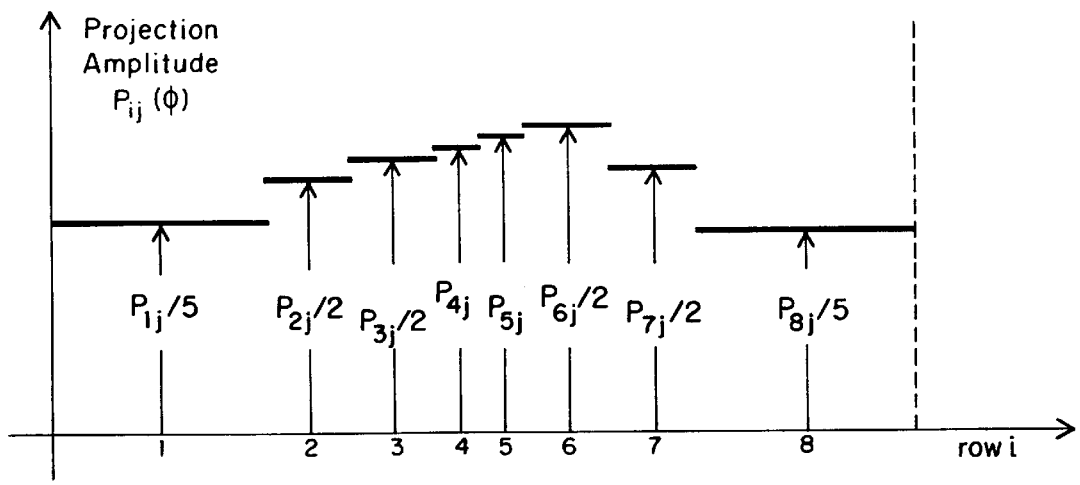
FIG. 8A is a chart of projection data collected from a non-equal height detector array having row heights corresponding to integer relationships, in accordance with the present invention.
Figure 8B:
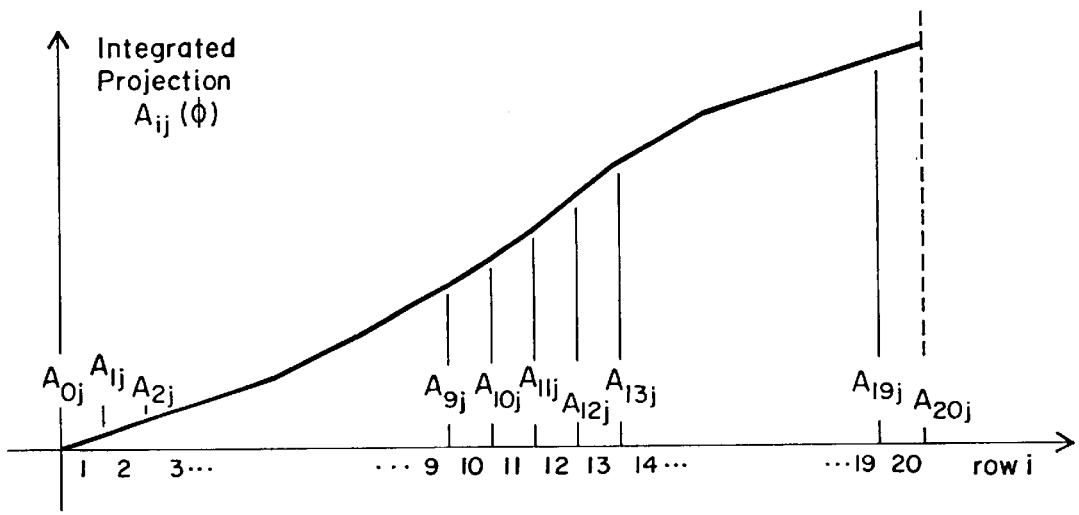
FIG. 8B is a chart of integrated projection data computed from the data of FIG. 8A, in accordance with the present invention.

Projection values $P_{ij}(\phi)$ for a non-equal height detector system are illustrated in FIG. 8A. The integrated projection values $A_{mj}(\phi)$ generated by Equation (15) in equal spacing are plotted in FIG. 8B. The locations i1 and i2, as well as the partial weights $w_{i1}$ and $w_{i2}$, are calculated according to the scale in the unit of $\Delta h$. The same calculations, given by Equations (12), (13), and (14), are used to compute for the re-sampling projection values $S_{kj}(\phi)$. A drawback of this integration method is the requirement that there exists a common factor $\Delta h$ among the heights of all detector rows. In the above-described example, the detector system comprises three different detector row heights of t, 2t, and 5t, and the common factor is $\Delta h=t$. For detector systems having different detector row heights of a non-integer ratio, for example the gradually increasing detector height system shown and described above with reference to FIG. 6, the following method is applicable.

Figure 9A:
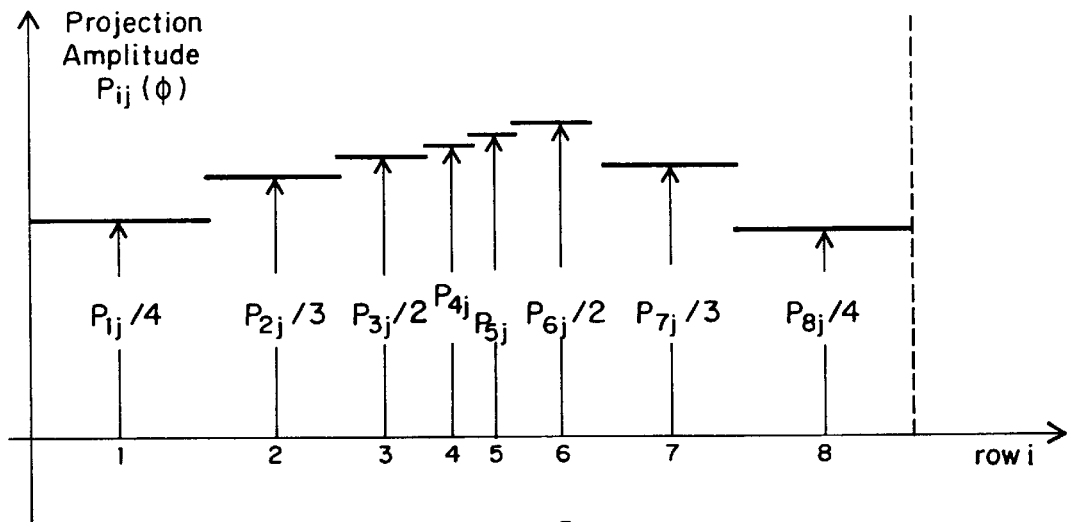
FIG. 9A is a chart of projection data collected by a detector array having progressively-, and gradually-varied row heights, in accordance with the present invention.
Figure 9B:
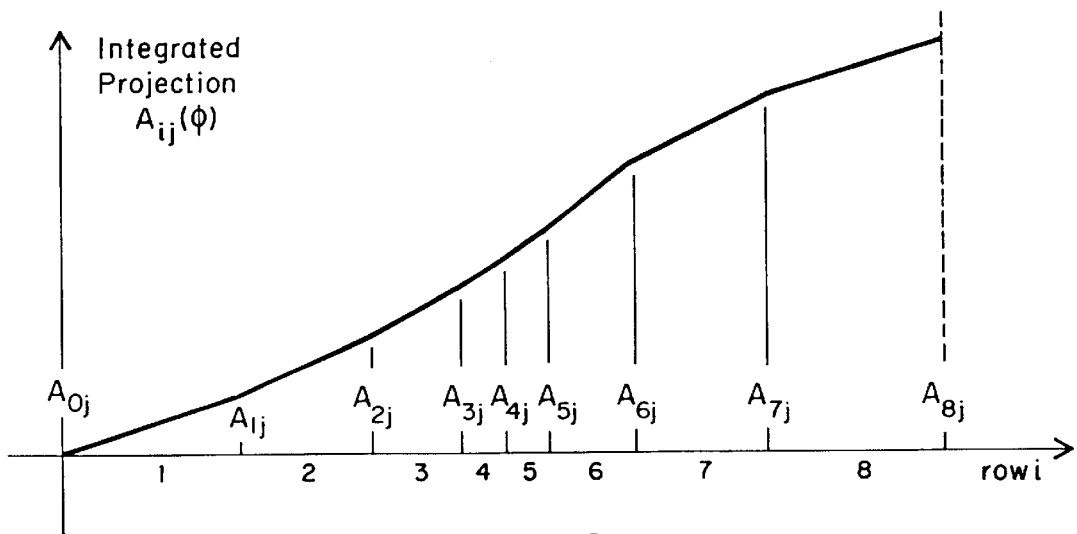
FIG. 9B is a chart of integrated projection data computed from the data of FIG. 9A, in accordance with the present invention.

In this method, the projection values $P_{ij}(\phi)$ collected from column j of M detectors are integrated according to:

$$A_{ij}(\phi)=A_{i-1,j}(\phi)+P_{ij}(\phi), \tag{16}$$

beginning with $A_{0j}(\phi)=0$, where $i=1, 2, \ldots, M$. FIGS. 9A and 9B are exemplary plots of the original projection values $P_{ij}(\phi)$ and the integrated projection values $A_{ij}(\phi)$, respectively, as a function of the z coordinate of the detector array. The integrated projection values $A_{ij}(\phi)$ are located at z coordinates of $h_0, h_1, h_2, \ldots, h_M$, in non-equal spacing. The location:

$$h_i=h_{i-1}\Delta h_i, \tag{17}$$

is the z coordinate of the boundary between detector row i−1 and row i.

A lookup table stored in a computer memory is preferably employed as efficient means to determine the z coordinates of the first and last rows, $i_1$ and $i_2$, having a non-zero weight for re-sampling, for a given detector column. The boundary positions of the reconstructing slice along detector column j, namely $z_{j1}(\phi)$ and $z_{j2}(\phi)$, are scaled in accordance with the z-coordinate scale of the lookup table, and truncated to integers as the address to the lookup table. The table provides the row number $i_1$ for $z_{j1}(\phi)$ and $i_2$ for $z_{j2}(\phi)$. A second lookup table containing the boundary z coordinate $h_{i-1}$ and the spacing $\Delta h_i$ for each row i can be used to calculate the starting and ending integrated projection values as:

$$A_{z1,j}(\phi)=A_{i1-1,j}(\phi)+(A_{i1,j}(\phi)-A_{i1-1,j}(\phi))(z_{j1}(\phi)-h_{i1-1})/\Delta h_{i1}. \tag{18}$$

$$A_{z2,j}(\phi)=A_{i2-1,j}(\phi)+(A_{i2,j}(\phi)-A_{i2-1,j}(\phi))(z_{j2}(\phi)-h_{i2-1})/\Delta h_{i2}. \tag{19}$$

Equations (18) and (19) can also be written as:

$$A_{z1,j}(\phi)=A_{i1-1,j}(\phi)+P_{i1,j}(\phi)(z_{j1}(\phi)-h_{i1-1})/\Delta h_{i1}, \text{ and} \tag{20}$$

$$A_{z2,j}(\phi)=A_{i2-1,j}(\phi)+P_{i2,j}(\phi)(z_{j2}(\phi)-h_{i2-1})/\Delta h_{i2}, \text{ and} \tag{21}$$

The re-sampled projection value $S_{kj}(\phi)$ of channel j at projection angle $\phi$ for slice k is then calculated as the difference between $A_{z1,j}(\phi)$ and $A_{z2,j}(\phi)$, as given in Equation (14).

In determining the corresponding row number i, from the scaled and truncated boundary position $z_{j1}(\phi)$, the lookup table may provide a row number of one less than $i_1$. This is because the lookup table is addressed to the truncated $z_{j1}(\phi)$, which may be of a different value than the corresponding row number of $z_{j1}(\phi)$ without truncation. As the precision of the lookup table increases, the truncation error is reduced and the likelihood of this discrepancy becomes smaller. Nevertheless, the possibility will exist of having a lookup row number of one less than the actual row number. When this occurs, the factor $(z_{j1}(\phi)-h_{i1-1})/\Delta h_{i1}$ from Equation (20) becomes slightly greater than 1.0, instead of the normal condition of less than 1.0. This means that instead of interpolating $A_{z1,j}(\phi)$ near the original sampling boundary point $h_{i1}$, $A_{z1,j}(\phi)$ is now extrapolated near $h_{i1}$ by the formulae of Equation (18) or (20). If the lookup table is large enough, $z_{j1}(\phi)$ should be very close to hi, when such a discrepancy occurs. In this case, the difference of the calculated results between extrapolation and interpolation is negligible. Likewise, the lookup row number $i_2$ may be one less than the actual row number corresponding to $z_{j2}(\phi)$, but this does not affect the calculation of the integrated projection value $\Delta z_{j2}(\phi)$ by Equation (19) or (21).

A method and apparatus for re-sampling from over-sampled projection data along the z-axis are proposed above for the purpose of minimizing the inconsistency in the slice thickness as measured in different detector channels and different projection angles of a helical scan. The image reconstructed from such re-sampled data offers an improvement in the slice profile and a reduction in reconstruction artifacts. By re-sampling the projection data prior to reconstruction, the present technique minimizes the calculations associated with reconstruction. For example in a preferred embodiment of the present invention, a single slice is reconstructed from data derived from the multiple over-sampled detector rows, in contrast with the requirement of reconstructing and combining multiple thinner slices according to the prior technique. The extent of oversampling is preferably moderate, such that the detector system does not contain an excessive number of rows.

The present invention is applicable to both equal-height detector configurations and non-equal height detector configurations and a combination of both, where some of the rows of detectors are of equal height and others not. Re-sampling can be performed on the original cone-beam data, in which the data collected by each row of detectors are in the form of fan-beam projections. Alternatively, re-sampling can also be performed following reordering of the fan-beam projections into parallel-beam projections.

In an equal-height detector system, it is preferred to set the equivalent isocenter detector height $\Delta h$ to be less than the thickness of the thinnest slice to be reconstructed. The projection data for substantially thick slices will be highly over-sampled, and thus generate a substantially improved image as compared to the prior techniques that do not employ over-sampling. In a non-equal height detector system, it is preferred to set the equivalent isocenter detector height $\Delta h_i$ of the middle rows (which have the least height) to be less than the thickness of the thinnest slice to be reconstructed. The projection data collected by the original rows are left uncombined, such that the data can be re-sampled from somewhat over-sampled projection data.

According to a standard detector geometry, the X-ray source and the middle row of detectors lie on a rotation plane (xy-plane) perpendicular to the z-axis, and each row of detectors is located on a circular path. For certain reconstruction methods of helical scans, the projection data required are not exactly measured by detectors located in circular paths, but rather in helical paths. Thus, it has been proposed to tilt the detector array by rotating it about the central X-ray beam by a small angle, such that the detectors of each row lie close to the helical path as described in U.S. patent application Ser. No. 09/095,554, filed Jun. 11, 1998, commonly owned with the present application, and U.S. Pat. No. 5,796,803, both being incorporated herein by reference in their entirety. In these modified detector array embodiments, the tilt angle is taken into account in determining the corresponding row locations of each column of the detector array for re-sampling of the projection data.

Further reconstruction techniques are applicable to the present invention, including the techniques described in the pending U.S. Patent Application entitled "Apparatus and Method for Reconstruction of Volumetric Images in a Helical Scanning Cone-Beam Computed Tomography System", by C. M. Lai Ser. No. 09/374,679, and "Apparatus and Method for Reconstruction of Images in a Computed Tomography Scanner Using Oblique Slices", by C. M. Lai Ser. No. 09/375,347, both filed on even date herewith and commonly owned with the present application, and both being incorporated herein by reference.

While this invention has been particularly shown and described with references to preferred embodiments thereof, it will be understood by those skilled in the art that various changes in form and in details may be made therein without departing from the spirit and scope of the invention as defined by the appended claims.

I claim:

1. A method of reconstructing an object image as successive slices of a predetermined slice thickness in a helical cone-beam computed tomography scanner, comprising:

over-sampling projection data with a two-dimensional detector array arranged in rows and columns, the array having at least some detector rows of a height less than the slice thickness;

re-sampling the projection data relative to a system translation axis according to the predetermined slice thickness to generate re-sampled projection data; and reconstructing the re-sampled projection data to generate an object image.

2. The method of claim 1 wherein over-sampling comprises over-sampling projection data with an equal height detector array.

3. The method of claim 1 wherein over-sampling comprises over-sampling projection data with a non-equal-height detector array.

4. The method of claim 3 wherein the detector rows comprise at least one middle row and outer rows, the row heights of the outer rows increasing progressively as their distance from the at least one middle row increases.

5. The method of claim 4 wherein the progressive increase of the outer row heights is according to integer multiples of the at least one middle row height.

6. The method of claim 1 wherein the progressive increase of the outer row heights is gradual with respect to the at least one middle row height.

7. The method of claim 1 wherein re-sampling comprises identifying the boundaries of each slice along the translation axis and summing the data values detected by detector rows between the boundaries.

8. The method of claim 7 further comprising identifying boundary detector rows containing the boundaries, and weighting the projection data collected by the boundary detector rows according to the position of the boundary with respect to the detector row along the translation axis.

9. The method of claim 1 wherein the slice is tilted at an oblique angle with respect to the translation axis.

10. The method of claim 1 wherein re-sampling further comprises integrating the projection data over all rows and re-sampling based on the integrated data values.

11. The method of claim 10 wherein integrating further comprises:

interpolating first and second boundary position values along the system translation axis based on the intersection of the slice and the detector rows; and subtracting the first and second boundary position values to determine the re-sampled projection data.

12. The method of claim 1 wherein re-sampling comprises selecting locations, with respect to the detector rows, of multiple slices to be re-sampled and reconstructed at a predetermined interval.

13. The method of claim 12 wherein the predetermined interval is selected to be equal to the predetermined slice thickness such that the reconstructed slices are contiguous.

14. The method of claim 12 wherein the predetermined interval is selected to be smaller than the predetermined slice thickness such that the reconstructed slices overlap.

15. The method of claim 12 wherein the predetermined interval is selected to be greater than the predetermined slice thickness such that the reconstructed slices are spaced apart.

16. A detector array for a computed tomography scanner including an energy source and said detector array for reconstructing an image of an object as multiple successive slices, said detector array comprising an array of detector elements arranged in longitudinal columns along a rotation axis, and in lateral rows along a lateral axis orthogonal to said longitudinal axis, outer rows of said array having a gradually increased height with respect to the heights of inner rows.

17. The detector array of claim 16 wherein the smallest detector row height is less than a predetermined thickness of the reconstructed slice.

18. The detector array of claim 16 wherein the detector rows lie along an arc substantially orthogonal to the system longitudinal axis.

19. The detector array of claim 18 wherein the arc is a semicircle centered at the energy source.

20. The detector array of claim 16 wherein the detector columns lie substantially parallel to the rotation axis.

21. A helical computed tomography scanner for reconstructing an object image as successive slices of a predetermined slice thickness, comprising:

a source that generates a cone-beam of radiation;

a two-dimensional detector array arranged in rows and columns, the array having at least some detector rows of a height less than the slice thickness, the object being irradiated by the cone beam in turn incident on the detector array to generate oversampled projection data; and a processor for re-sampling the oversampled projection data relative to a system translation axis according to the predetermined slice thickness to generate re-sampled projection data, and for reconstructing the re-sampled projection data to generate an object image.

22. The helical computed tomography scanner of claim 21 wherein the detector array includes rows of equal height.

23. The helical computed tomography scanner of claim 21 wherein the detector array includes at least two rows of unequal height.

24. The helical computed tomography scanner of claim 23 wherein the detector rows comprise at least one middle row and outer rows, the row heights of the outer rows increasing progressively as their distance from the at least one middle row increases.

* * * * *